United States Patent [19]

Horovitz et al.

[11] 4,217,347
[45] Aug. 12, 1980

[54] METHOD OF TREATING HYPERTENSION AND MEDICAMENTS THEREFOR

[75] Inventors: Zola P. Horovitz, Princeton; Bernard Rubin, Lawrence Township, Cumberland County, both of N.J.

[73] Assignee: E. R. Squibb & Sons, Inc., Princeton, N.J.

[21] Appl. No.: 958,062

[22] Filed: Nov. 9, 1978

Related U.S. Application Data

[63] Continuation-in-part of Ser. No. 864,428, Dec. 27, 1977, abandoned.

[51] Int. Cl.² .................. A61K 31/54; A61K 31/415
[52] U.S. Cl. ............................ 424/246; 424/274
[58] Field of Search .............................. 424/274, 246

[56] References Cited

U.S. PATENT DOCUMENTS

| | | | |
|---|---|---|---|
| 3,081,230 | 3/1964 | Weinstock et al. | 424/246 |
| 3,137,625 | 6/1964 | Biel | 424/246 |
| 4,046,889 | 9/1977 | Ondetti | 424/274 X |

OTHER PUBLICATIONS

Ondetti, et al., "Design of Specific Inhibitors of Angiotensin-Converting Enzyme . . . ", Science 196,441, 1977.

Johnson et al., "Treatment of Patients With Severe Hypertension by Inhibition of Angiotensin-converting Enzyme"-Clin. Sci. vol. Med. 48:53s, 1975.

Physicians Desk Reference, 31 Edition, 1977, P. 507.

Wollen et al., "Antihypertensive Drugs: Clinical Pharmacology and Therapeutic Use"-Drugs 14:420-460, (1977).

Primary Examiner—Stanley J. Friedman
Attorney, Agent, or Firm—Lawrence S. Levinson; Donald J. Barrack

[57] ABSTRACT

A method for reducing blood pressure comprises administering a combination of a diuretic compound and a compound having the general formula

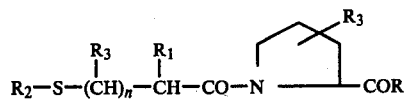

25 Claims, No Drawings

METHOD OF TREATING HYPERTENSION AND MEDICAMENTS THEREFOR

This application is a continuation-in-part of application Ser. No. 864,428, filed Dec. 27, 1977 and now abandoned.

SUMMARY OF THE INVENTION

The present invention relates to a method for reducing or alleviating hypertension with a combination comprising an effective amount of a compound of the fomula

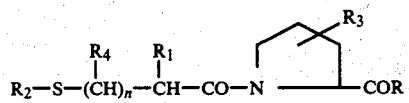

wherein:
R is hydroxy, lower alkoxy or $NH_2$;
$R_1$ and $R_4$ each is hydrogen, lower alkyl or phenyl-lower alkyl;
$R_2$ is hydrogen or $R_5$-CO;
$R_3$ is hydrogen, hydroxy or lower alkyl;
$R_5$ is lower alkyl, phenyl or phenyl-lower alkyl; and
n is 0, 1 or 2.
with an effective amount of a diuretic compound and such a combination of medicaments.

DETAILED DESCRIPTION OF THE INVENTION

The compounds of formula I have been reported to be angiotensin converting enzyme inhibitors which intervene in the angiotensinogen→renin→angiotensin I→angiotensin II mechanisn and are effective in reducing or alleviating hypertension. See U.S. Pat. No. 4,046,889, Sept. 6, 1977; Science 196, 441–443 (1977). It has been found that such compounds can be used in an oral dosage range of about 0.1 to 100 mg/kg per day and are most effective when provided at a total daily dosage of about 60 to 600 mg. Dosages within this range achieve a substantial reduction in arterial blood pressure and, in most instances, little, if any significant reduction is obtained by further increasing the dosage. Although certain peptides, teprotide (SQ20,881) for example, have been reported to have angiotensin converting enzyme activity, they are not of practical use for such an indication because of the cost and particularly since they are ineffective when orally administered [Rubin et al., 204, Jour. Pharm. Exper. Ther. 271–280, 1978; Laffan et al., Jour. Pharm. Exper. Ther. 204, 281–288, 1978; Brit. Med. Jour. 2(6141):866, 1978].

Hypertension is also frequently treated by the administration of a diuretic. Typically, treatment with an antihypertensive agent alone results in a compensatory retention of sodium and water which concomitant administration of a diuretic prevents (Wollam et al., Drugs 14:420-460, 1977). However, administration of a compound of formula I does not result in sodium and water retention when administered alone and, in fact, may by itself cause natriuresis and diuresis (Bengis et al, Circulation Research, Vol. 43 I-45-I-53, 1978). Therefore, a diuretic would not be expected to enhance the antihypertensive action of compounds of formula I. However, it has been demonstrated that the administration of a diuretic in combination with compounds of formula I is more effective than either drug alone. The combination of such compounds with a diuretic as described below results in a potentiation of the reduction in blood pressure significantly beyond that level which either substance can achieve itself at a dosage within the acceptable range and also at lower dosage levels.

This invention therefore relates to a combination of a compound having formula I above and a diuretic of the group consisting of the thiazide class, e.g., chlorothiazide, hydrochlorothiazide, flumethiazide, hydroflumethiazide, bendroflumethiazide, methychlothiazide, trichlormethiazide, polythiazide or benzthiazide, as well as ethacrynic acid, ticrynafen, chlorthalidone, furosemide, bumetanide, triamterene, amiloride and spironolactone, and salts of such compounds, compositions comprising a combination of such compounds and to a method for alleviating hypertension with a combination of compounds.

Preferred are those compounds of formula I wherein R is hydroxy or lower alkoxy, especially $C_1$–$C_4$ lower alkoxy; $R_1$ is hydrogen or lower alkyl, especially methyl, $R_2$ is hydrogen or lower alkanoyl, especially $C_2$–$C_4$ lower alkanoyl; $R_3$ is hydrogen or hydroxy, especially 4-hydroxy; $R_4$ is hydrogen or lower alkyl, especially $C_1$–$C_4$ lower alkyl; and n is 0 or 1. Especially preferred in this group are compounds of formula I wherein R is hydroxy; $R_1$ is hydrogen or methyl; $R_2$ is hydrogen or acetyl; $R_3$ is hydrogen; $R_4$ is hydrogen or methyl; and n is 0 or 1. The especially preferred embodiment includes a compound of formula I wherein R is hydroxy; $R_1$ is methyl; $R_2$, $R_3$ and $R_4$ each is hydrogen; and n is 1, most especially (D-3-mercapto-2-methylpropanoyl)-L-proline.

Preferred as the second component of the combination is chlorothiazide, hydrochlorothiazide, furosemide, ticrynafen or triamterene, especially hydrochlorothiazide or furosemide.

The especially preferred embodiments are compositions comprising (D-3-mercapto-2-methyl-propanoyl)-L-proline with either hydrochlorothiazide or furosemide.

The compounds of formula I can be produced as described in U.S. Pat. No. 4,046,889, Sept. 6, 1977. The diuretic members of the combination are known compounds which are produced by methods described in the literature.

According to this invention, a combination of a compound of formula I and a diuretic is administered in an effective amount which comprises a total daily dosage of about 30 to 600 mg., preferably 30 to 300 mg. of a compound of formula I and about 15 to 300 mg. preferably 15 to 200 mg. of the diuretic to a mammalian species which has elevated blood pressure. Such total daily dosages can be used in a single administration of the total amount or in divided doses two to four times daily. Generally, a t.i.d. or q.i.d. regimen is preferred. This preferred dosage is about 10 to 100 mg. of the compound of formula I and about 5 to 75 mg. of the diuretic three times daily or about 5 to 125 mg. of the compound of formula I and about 2.5 to 50 mg. of the diuretic four times daily. The preferred route of administration is oral.

According to one preferred embodiment, the substances can be formulated in a single pharmaceutical dosage form for oral administration such as tablet, capsule, solution or suspension comprising an effective amount of each of the active ingredients in a physiologically acceptable carrier therefor.

The active substances in the dosage unit are present in a ratio of about 1:2 to about 12:1, preferably about 2.5:1 to about 10:1, of the compound of formula I with respect to the diuretic (by weight). Generally, about 10 to 200 mg. of a compound of formula I and about 2.5 to 100 mg. of the second component can be readily formulated in the composition.

Tablets of various sizes can be prepared, e.g., of about 50 to 700 mg. in total weight, containing the active substances in the ranges described above, with the remainder being a physiologically acceptable carrier or other materials according to accepted pharmaceutical practice. These tablets can, of course, be scored to provide for fractional doses. Gelatin capsules can be similarly formulated.

Liquid formulations can also be prepared by dissolving or suspending the combination of active substances in a conventional liquid vehicle acceptable for pharmaceutical administration so as to provide the desired dosage in one to four teaspoonsful.

Such dosage forms can be administered to the patient on a regimen of one to four doses per day.

According to another modification, in order to more finely regulate the dosage schedule, the substances may be administered separately in individual dosage units at the same time or carefully coordinated times. Since blood levels are built up and maintained by a regulated schedule of administration, the same result is achieved by the simultaneous presence of the two substances. The respective substances can be individually formulated in separate unit dosage forms in a manner similar to that described above.

Fixed combinations of the compound of formula I and the diuretic are more convenient and are preferred, expecially in tablet or capsule form for oral administration.

In formulating the compositions of this invention the active substances, in the amounts described above, are compounded according to accepted pharmaceutical practice with a physiologically acceptable vehicle, carrier, excipient, binder, preservative, stabilizer, flavor, etc., in the particular type of unit dosage form.

Illustrative of the adjuvants which may be incorporated in tablets are the following: a binder such as gum tragacanth, acacia, corn starch or gelatin; an excipient such as dicalcium phosphate or cellulose; a disintegrating agent such as corn starch, potato starch, alginic acid or the like; a lubricant such as stearic acid or magnesium stearate; a sweetening agent such as sucrose, lactose or saccharin; a flavoring agent such as orange, peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup or elixir may contain the active compound, water, alcohol or the like as the carrier, glycerol as solubilizer, sucrose as sweetening agent, methyl and propyl parabens as preservatives, a dye and a flavoring such as cherry or orange.

Many of the active substances described above form commonly known, pharmaceutically acceptable salts such as alkali metal and other common basic salts or acid addition salts, etc. References to the base substances are therefore intended to include those common salts known to be substantially equivalent to the parent compound.

The following examples are illustrative of the invention and constitute especially preferred embodiments. They also serve as models for the preparation of other members of the group which can be produced by suitable substitution of ingredients as described above.

EXAMPLE 1

6000 tablets each containing the following ingredients:

| | | |
|---|---|---|
| (D-3-mercapto-2-methylpropanoyl)-L-proline | 100 | mg. |
| Avicel (microcrystalline cellulose) | 100 | mg. |
| Hydrochlorothiazide | 12.5 | mg. |
| Lactose U.S.P. | 113 | mg. |
| Corn starch U.S.P. | 17.5 | mg. |
| Stearic acid U.S.P. | 7 | mg. |
| | 350 | mg. | are produced (from sufficient bulk quantities) by slugging the (D-3-mercapto-2-methylpropanoyl)-L-proline, Avicel and a portion of the stearic acid. The slugs are ground and passed through a #2 screen, then mixed with the hydrochlorothiazide, lactose, corn starch and remainder of the stearic acid. The mixture is compressed into 350 mg. capsule shaped tablets in a tablet press. The tablets are scored for dividing in half.

EXAMPLE 2

10,000 tablets each containing the following ingredients:

| | | |
|---|---|---|
| (D-3-mercapto-2-methylpropanoyl)-L-proline | 200 | mg. |
| Corn starch U.S.P. | 17.5 | mg. |
| Lactose U.S.P. | 215.4 | mg. |
| Acacia U.S.P. | 10.6 | mg. |
| Water qs | (ca. 0.03 ml.) | |
| Hydrochlorothiazide | 25 | mg. |
| Corn starch U.S.P. | 17.5 | mg. |
| Avicel | 200 | mg. |
| Stearic Acid | 14 | mg. |
| | 700 | mg. | are produced from sufficient bulk quantities as follows:

The acacia is dissolved in water. 17.5 mg. of corn starch, the (D-3-mercapto-2-methylpropanoyl)-L-proline and lactose are mixed thoroughly. The dry mixture is granulated using the aqueous solution of acacia. The granulation is wet screened, dried at 120° F. and reduced. The reduced, dry granulation is mixed with the hydrochlorothiazide and the remaining excipients are then added and mixed. The mixture is compressed into tablets of 700 mg. each.

EXAMPLE 3

Tablets each containing the following ingredients are made as described in Example 2:

| | | |
|---|---|---|
| (D-3-mercapto-2-methylpropanoyl)-L-proline | 75 | mg. |
| Corn starch U.S.P. | 8 | mg. |
| Lactose U.S.P. | 120 | mg. |
| Acacia U.S.P. | 6 | mg. |
| Water qs. | (ca. 0.03 ml.) | |
| Chlorothiazide | 50 | mg. |
| Corn starch U.S.P. | 8 | mg. |
| Avicel | 75 | mg. |
| Stearic acid | 8 | mg. |

-continued

|  |  |  |
|---|---|---|
|  | 350 | mg. |

EXAMPLE 4

1000 capsules, each containing the following ingredients:

|  |  |  |
|---|---|---|
| (D-3-mercapto-2-methylpropanoyl)-L-proline | 100 | mg. |
| Lactose U.S.P. | 211.8 | mg. |
| Magnesium stearate | 3.2 | mg. |
| Hydrochlorothiazide | 10 | mg. |
|  | 325 | mg. | are produced by dry blending the bulk materials (except the magnesium stearate) in a Hobart mixer, then passing the blend through a #20 screen. The materials are mixed again in the Hobart mixer with the magnesium stearate. The mixture is then filled into #2 two-piece gelatin capsules.

EXAMPLE 5

By substituting 10 mg. of furosemide for the hydrochlorothiazide in Example 4, capsules containing furosemide and (D-3-mercapto-2-methylpropanoyl)-L-proline are similarly produced.

EXAMPLE 6

By following the proceudre of Example 2 but substituting 20 mg. of furosemide for the hydrochlorothiazide and using 220.4 mg. of lactose, 700 mg. tablets each containing 20 mg. of furosemide and 200 mg. of (D-3-mercapto-2-methylpropanoyl)-L-proline are similarly produced.

EXAMPLE 7

By substituting 10 mg. of furosemide for the hydrochlorothiazide and using 115.5 mg. of lactose in the procedure of Example 1, 350 mg. scored tablets each containing 10 mg. of furosemide and 100 mg. of (D-3-mercapto-2-methylpropanoyl)-L-proline are similarly produced.

EXAMPLE 8

6000 scored tablets of 400 mg. each and containing the following ingredients:

|  |  |  |
|---|---|---|
| (D-3-mercapto-2-methylpropanoyl)-L-proline | 125 | mg. |
| Corn starch | 8 | mg. |
| Lactose U.S.P. | 95 | mg. |
| Acacia | 7 | mg. |
| Water qs. | (ca. 0.03 ml.) | |
| Triamterene | 50 | mg. |
| Corn starch U.S.P. | 8 | mg. |
| Avicel | 100 | mg. |
| Stearic acid | 7 | mg. |
|  | 400 | mg. | are produced as described in Example 2.

EXAMPLE 9

6000 scored tablets of 350 mg. each and containing the following ingredients:

|  |  |  |
|---|---|---|
| (D-3-mercapto-2-methylpropanoyl)-L-proline | 100 | mg. |
| Avicel | 100 | mg. |
| Triamterene | 25 | mg. |
| Lactose U.S.P. | 100 | mg. |
| Corn starch U.S.P. | 17 | mg. |
| Stearic acid | 8 | mg. |
|  | 350 | mg. | are produced as described in Example 1.

EXAMPLE 10

5000 scored tablets of 180 mg. each and containing the following ingredients:

|  |  |  |
|---|---|---|
| (D-3-mercapto-2-methylpropanoyl)-L-proline | 10 | mg. |
| Avicel | 50 | mg. |
| Hydrochlorothiazide | 5 | mg. |
| Lactose U.S.P. | 101 | mg. |
| Corn starch U.S.P. | 10 | mg. |
| Stearic acid | 4 | mg. |
|  | 180 | mg. | are produced as described in Example 1.

EXAMPLE 11

By substituting the same amount of ticrynafen for the hydrochlorothiazide in Example 1, tablets containing 100 mg. of (D-3-mercapto-2-methylpropanoyl)-L-proline and 12.5 mg. of ticrynafen are similarly obtained.

Representative of the results obtained with combinations of agents of this invention are data obtained from studies in spontaneously hypertensive rats and two kidney renal hypertensive rats.

(A) In an acute study with spontaneously hypertensive rats, ten to fourteen week old male Wistar-Kyoto spontaneously hypertensive rats (190–210 gm.) of the Okamoto-Aoki strain (obtained from Taconic Farms, Germantown, N.Y.) were given food and water ad libitum and intubated according to the method of Weeks and Jones, Proc. Soc. Exp. Biol. Med. 104, 646–648 (1960), to prepare them for blood pressure and heart rate determination by implanting indwelling abdominal aortic catheters under sodium pentobarbital anesthesia.

Three weeks later their direct blood pressure and heart rate were recorded by the method of Laffan et al., Cardiovasc. Res. 6, 319–324 (1972), modified as follows. The signal from the transducer was digitized in a 10 bit A/D converter and input to a PDP 11/05 computer. The computer was programmed to sense and store samples at a rate of 125/sec for each rat, as well as the number of pressure pulses during 10 sec. of each scan on each rat. These parameters were averaged and stored as the MBP (mean blood pressure, mm Hg) and heart rate (beats/min.) for that time. Data were acquired from each rat every five minutes. Six such sets of data were averaged to give a mean value representing a 30 minute sample and this 30 minute figure was stored for subsequent analysis. Each time a 48 hour cycle was completed (or sooner if demanded) the data were transferred serially to a host computer (PDP 11/40) for further analysis and the data were printed out on a Versatec Printer/Plotter for at least 16 hours after each dose.

The spontaneously hypertensive rats were segregated into four groups of five rats each (except group 3 which included six rats). The following was administered to the rats in the respective groups:

1. (Control) Agar-5 ml./kg+agar-5 ml./kg
2. Water-5 ml./kg+Compound A-30 mg./kg
3. Compound F**-50 mg./kg+Agar-5 ml./kg
4. Compound F**-50 mg./kg+Compound A*-30 mg./kg

* Compound A=(D-3-mercapto-2-methylpropanoyl)-L-proline
** Compound F=Furosemide Compound F was suspended in 0.25% agar and Compound A was in aqueous solution. All substances were administered by gavage and there was a one hour interval between drugs. Test results were evaluated 2.5 hours after single oral doses.

The following results were obtained:

TABLE I

| | Mean Blood Pressure (mm/Hg) | |
|---|---|---|
| | Before | 2.5 hours after single oral dose |
| (1) | 173 | 169 |
| (2) | 175 | 158 |
| (3) | 184 | 172 |
| (4) | 177 | 128 |

In these studies Compound F alone, 50 mg./kg. p.o., produced a 9.7% decrease in SHR blood pressure. Compound A alone, 30 mg./kg., produced 6.5% decrease in blood pressure. The combination of Compound A, 30 mg./kg., p.o., +Compound B, 50 mg./kg., p.o., reduced blood pressure in SHR rats by 27.7%.

(B) In chronic studies with renal hypertensive rats, male rats (115-150 g.) of the Charles River Sprague Dawley (COBS-CO) strain were anesthetized with ether and a silver clip (0.22 mm i.d.) was placed on the left renal artery through a flank incision. The contralateral kidney was left intact (two-kidney Goldblatt model: 2-K RHR). Each rat was fitted with a tail cuff for air inflation and a Korotkoff sound microphone for the detection of arterial pulsation. An oscilloscope was used for a visual appearance and disappearance of the pulse. Blood pressure measurements were determined after a minimum of six inflations with systolic pressures observed on a Narco physiograph manometer. Blood pressures were determined initially just prior to dosing and twice weekly at 4 hours after dosing.

The number of rats in each group was 15. Single daily treatments were made by gavage with crossover treatments as indicated in the table below. The control group received distilled water. Compound A was administered in distilled water, 30 mg./kg. Compound H was administered in 0.25% methylcellulose. The means blood pressure (mm/Hg.) for each group before dosing and on day 119 (4 hours after dosing) and the number of survivors on day 120 is shown in the table.

TABLE II

| Group | Treatment | Crossover Treatment* | Mean Blood Pressure Initial | Mean Blood Pressure Day 119 | No. of Survivors (%) | |
|---|---|---|---|---|---|---|
| 1 | H₂O | H₂O | 198 ± 4.9 | 207 ± 6.6 | 10 | (66.7) |
| 2 | H₂O | H₂O + A | 198 ± 4.9 | 206 ± 5.2 | 10 | (66.7) |
| 3 | H₂O | H₂O + H | 206 ± 7.5 | 207 ± 4.8 | 11 | (73.3) |
| 4 | A | A | 197 ± 5.3 | 167 ± 4.6 | 14 | (93.3) |
| 5 | A | H₂O | 197 ± 6.2 | 176 ± 5.1 | 14 | (93.3) |
| 6 | A | A# + H# | 202 ± 6.6 | 140 ± 4.6 | 15 | (100) |
| 7 | H | H | 197 ± 5.8 | 202 ± 8.4 | 8 | (53.3) |

*Crossover took place on day 28 through day 33 and on day 91 through day 96 (except Group 6 - see below).
Daily dosage of each maintained from day 109 on.
A = (D-3-mercapto-2-methylpropanoyl)-L-proline
H = Hydrochlorothiazide The foregoing data show that on long term treatment compound H shows no significant decrease in blood pressure. Compound A alone shows approximately a 10 to 15% reduction in blood pressure. The combination dosing with Compound A and Compound H shows approximately a 30% reduction in blood pressure. Moreover, the combination is the only one showing a 100% survivor rate.

What is claimed is:

1. A method for reducing blood pressure which comprises orally administering to a mammalian species having elevated blood pressure a daily dosage of a combination comprising about 30 to 600 mg. of a compound having the formula

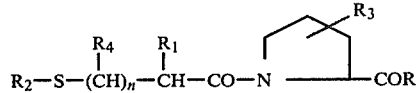

wherein:
R is hydroxy, lower alkoxy or NH₂;
R₁ and R₄ each is hydrogen, lower alkyl or phenyl-lower alkyl;
R₂ is hydrogen or R₅-CO;
R₃ is hydrogen, hydroxy or lower alkyl;
R₅ is lower alkyl, phenyl or phenyl-lower alkyl; and
n is 0, 1 or 2 and about 15 to 300 mg. of a diuretic selected from the group consisting of chlorothiazide, hydrochlorothiazide, flumethiazide, amiloride, hydroflumethiazide, bendroflumethiazide, methyclothiazide, trichlormethiazide, polythiazide, benzthiazide, ethacrynic acid, ticrynafen, chlorthalidone, furosemide, bumetanide, triamterene and spironolactone or salts of said compounds.

2. A method as in claim 1 wherein the combination comprises about 30 to 300 mg. of the compound of the formula and about 15 to 200 mg. of the diuretic.

3. A method as in claim 1 wherein the compound of the formula has R as hydroxy or lower alkoxy; R₁ as hydrogen or lower alkyl; R₂ as hydrogen or lower alkanoyl; R₃ as hydrogen or hydroxy; R₄ as hydrogen or lower alkyl; and n as 0 or 1.

4. A method as in claim 1 wherein the compound of the formula has R as hydroxy; R₁ as hydrogen or methyl; R₂ as hydrogen or acetyl; R₃ as hydrogen; R₄ as hydrogen or methyl; and n as 0 or 1.

5. A method as in claim 1 wherein the diuretic is chlorothiazide, hydrochlorothiazide, furosemide, ticrynafen or triameterene.

6. A method as in claim 1 wherein the diuretic is hydrochlorothiazide or furosemide.

7. A method as in claim 1 wherein the compound of the formula has R as hydrogen or lower alkoxy; $R_1$ as hydrogen or lower alkyl; $R_2$ as hydrogen or lower alkanoyl; $R_3$ as hydrogen or hydroxy; $R_4$ as hydrogen or lower alkyl; and n as 0 or 1; and the diuretic is chlorothiazide, hydrochlorothiazide, furosemide, ticrynafen or triamterene.

8. A method as in claim 1 comprising about 30 to 300 mg. of a compound of the formula wherein R is hydroxy or lower alkoxy; $R_1$ and $R_4$ each is hydrogen or lower alkyl; $R_2$ is hydrogen or lower alkanoyl, $R_3$ is hydrogen or hydroxy; and n is 0 or 1, and about 15 to 200 mg. of chlorothiazide, hydrochlorothiazide, furosemide, ticrynafen or triamterene.

9. A method as in claim 1 wherein the compound of the formula is (D-3-mercapto-2-methylpropanoyl)-L-proline and the diuretic is hydrochlorothiazide or furosemide.

10. A method as in claim 1 wherein the compound of the formula is (D-3-mercapto-2-methylpropanoyl)-L-proline in an amount of about 30 to 300 mg. and the diuretic is hydrochlorothiazide in an amount of about 15 to 200 mg.

11. A method as in claim 1 wherein the compound of the formula is (D-3-mercapto-2-methylpropanoyl)-L-proline in an amount of about 30 to 300 mg. and the diuretic is furosemide in an amount of about 15 to 200 mg.

12. An oral antihypertensive composition comprising about 30 to 600 mg. of a compound of the formula

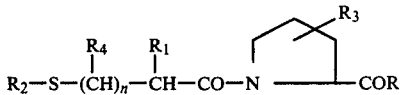

wherein:
R is hydroxy, lower alkoxy or $NH_2$;
$R_1$ and $R_4$ each is hydrogen, lower alkyl or phenyl-lower alkyl;
$R_2$ is hydrogen or $R_5$-CO;
$R_3$ is hydrogen, hydroxy or lower alkyl;
$R_5$ is lower alkyl, phenyl or phenyl-lower alkyl;
n is 0, 1 or 2,
about 15 to 300 mg. of a diuretic selected from the group consisting of chlorothiazide, hydrochlorothiazide, amiloride, flumethiazide, hydroflumethiazide, bendroflumethiazide, methylclothiazide, trichlormethiazide, polythiazide, benzthiazide, ethacrynic acid, ticrynafen, chlorthalidone, furosemide, bumetanide, triamterene, spironolactone and salts thereof, and a physiologically acceptable carrier therefor.

13. A composition as in claim 12 comprising about 30 to 300 mg. of the compound of the formula and about 15 to 200 mg. of the diuretic.

14. A composition as in claim 12 wherein the compound of the formula has R as hydroxy or lower alkoxy; $R_1$ as hydrogen or lower alkyl; $R_2$ as hydrogen or lower alkanoyl; $R_3$ as hydrogen or hydroxy; $R_4$ as hydrogen or lower alkyl; and n as 0 or 1.

15. A composition as in claim 12 wherein the compound of the formula has R as hydroxy; $R_1$ as hydrogen or methyl; $R_2$ as hydrogen or acetyl; $R_3$ as hydrogen; $R_4$ as hydrogen or methyl; and n as 0 or 1.

16. A composition as in claim 12 wherein the diuretic is chlorothiazide, hydrochlorothiazide, furosemide, ticrynafen or triamterene.

17. A composition as in claim 12 wherein the diuretic is hydrochlorothiazide or furosemide.

18. A composition as in claim 12 wherein the compound of the formula has R as hydrogen or lower alkoxy; $R_1$ as hydrogen or lower alkyl; $R_2$ as hydrogen or lower alkanoyl; $R_3$ as hydrogen or hydroxy; $R_4$ as hydrogen or lower alkyl; and n as 0 or 1; and the diuretic is chlorothiazide, hydrochlorothiazide, furosemide, ticrynafen or triamterene.

19. A composition as in claim 12 wherein the compound of the formula is (D-3-mercapto-2-methylpropanoyl)-L-proline and the diuretic is hydrochlorothiazide or furosemide.

20. A composition as in claim 12 comprising about 30 to 300 mg. of (D-3-mercapto-2-methylpropanoyl)-L-proline and about 15 to 200 mg. of hydrochlorothiazide.

21. A composition as in claim 13 comprising about 30 to 300 mg. of (D-3-mercapto-2-methylpropanoyl)-L-proline and about 15 to 200 mg. of furosemide.

22. A composition as in claim 25 comprising about 5 to 125 mg. of (D-3-mercapto-2-methylpropanoyl)-L-proline and about 2.5 to 50 mg. of hydrochlorothiazide.

23. A composition as in claim 25 comprising about 5 to 125 mg. of (D-3-mercapto-2-methylpropanoyl)-L-proline and about 2.5 to 50 mg. of furosemide.

24. An oral hypertensive composition comprising about 5 to 125 mg. of (D-3-mercapto-2-methylpropanoyl)-L-proline and about 5 to 75 mg. of triamterene.

25. An oral antihypertensive composition comprising about 5 to 125 mg. of a compound of the formula

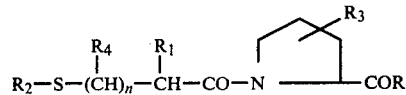

wherein:
R is hydroxy, lower alkoxy or $NH_2$;
$R_1$ and $R_4$ each is hydrogen, lower alkyl or phenyl-lower alkyl;
$R_2$ is hydrogen or $R_5$-CO;
$R_3$ is hydrogen, hydroxy or lower alkyl;
$R_5$ is lower alkyl, phenyl or phenyl-lower alkyl; and
n is 0, 1 or 2, about 2.5 to 50 mg. of a diuretic selected from the group consisting of chlorothiazide, hydrochlorothiazide, amiloride, flumethiazide, hydroflumethiazide, bendroflumethiazide, methylclothiazide, trichlormethiazide, polythiazide, benzthiazide, ethacrynic acid, ticrynafen, chlorthalidone, furosemide, bumetanide, triamterene, spironolactone and salts thereof, and a physiologically acceptable carrier therefor.

* * * * *

UNITED STATES PATENT OFFICE
CERTIFICATE OF CORRECTION

Patent No. 4,217,347   Dated August 12, 1980

Inventor(s) Zola P. Horovitz, et al

It is certified that error appears in the above-identified patent and that said Letters Patent are hereby corrected as shown below:

Column 2, line 38, delete the hyphen between methyl and propanoyl

Column 7, line 21, insert a * above the "A"

Column 7, line 68, "means" should read --mean--

Signed and Sealed this

Third Day of February 1981

[SEAL]

Attest:

RENE D. TEGTMEYER

Attesting Officer   Acting Commissioner of Patents and Trademarks